Nov. 3, 1959 R. W. CUMMING Plant Pat. 1,877
CHRYSANTHEMUM PLANTS
Filed July 5, 1957
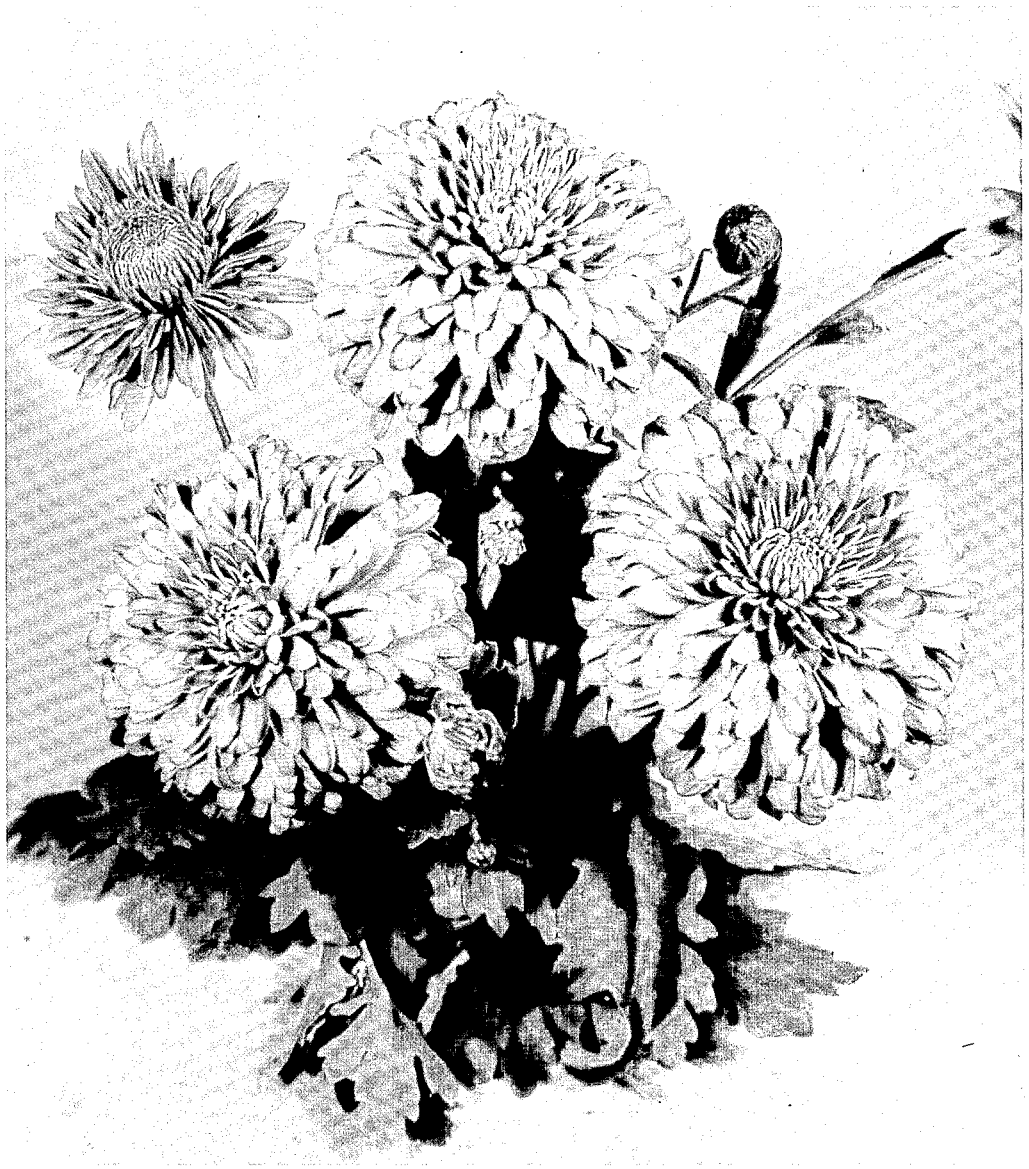
INVENTOR
Roderick W. Cumming
By Orville M Kile
Plant Pat. Agent.

United States Patent Office

Plant Pat. 1,877
Patented Nov. 3, 1959

1,877

CHRYSANTHEMUM PLANTS

Roderick W. Cumming, Bristol, Conn., assignor to Bristol Nurseries, Inc., Bristol, Conn.

Application July 5, 1957, Serial No. 670,353

1 Claim. (Cl. 47—60)

My present invention relates to a new and distinct variety of chrysanthemum in what is known as the "decorative" class. It was originated by me at our nurseries in Bristol, by crossing two unnamed, unpatented seedlings of red and bronze ancestry, respectively.

The primary objective of this cross was to produce a new chrysanthemum variety of undoubted vigor, and with an especially intense shade of bronze flower. These objectives were achieved, along with the following characteristics displayed by the new variety:

(1) The very free habit of blooming on broad, stalwart plants;

(2) The lush, ample light-green foliage, which remains on the plant all the way to the ground;

(3) The stiff, branching stems erectly borne;

(4) The fine productivity, decorative form, long season and cutflower virtues of the flowers;

(5) The distinct, vivid Dragon's Blood Red to Ochracious-Buff coloring of the flowers, impressing as a scarlet-bronze tonality to onlookers;

(6) The splendid winter hardiness of the plant.

The foregoing characteristics and distinctions definitely differentiate my new variety from its parents, as well as from all other varieties of its class of which I am aware. Asexual reproduction of my new variety by means of top cuttings, performed by me at Bristol, Connecticut, shows that these characteristics and distinctions come true to form and are established and transmitted through succeeding propagations.

The accompanying illustration shows typical specimens of the vegetative growth and flowers of my new chrysanthemum variety in various stages of development, depicted in color as nearly true as it is reasonably possible to make the same in a color illustration of this character.

Following is a detailed description of my new variety, with color terminology in accordance with Ridgway's Color Standards and Nomenclature.

Parentage: Two unnamed red seedlings, one of much bronze ancestry.

Cold resistance: Winter hardy in central Connecticut even without protection; flowers very frost-resistant.

Blooming period: In the Bristol, Connecticut area blooming starts about September 25 and continues until severe freezing weather.

Blooming habit: Very prolific bloomer over a long season. Produces well-formed flowers in splendid sprays.

Growth habit: Free, strong and branching, growing erectly to a height of from 24 to 30 inches.

Form: Compact, with abundant foliage all the way to the ground.

Stems: Strong, stiff, upright and branching.

Foliage:

*Quantity.*—Averages above normal.

*Persistence.*—Foliage remains on plant all the way to the ground.

*Size.*—Large. A typical mature leaf measures approximately 3 inches long and 2 inches across.

*Shape.*—Lobes and edges both rounded. Deeply lobed, with cuts almost to the midrib in most instances.

*Color.*—Upper surface approximately Deep Dull Yellow Green (Pl. XXXII). Under surface Light Cress Green (Pl. XXXI).

*The flower*

Observations for this description were made from specimens grown in a field at Bristol, Connecticut, mid-morning, in early October.

Bud:

*Size.*—Small.

*Shape.*—Flat and bulging.

*Opening.*—Opens slowly.

*Color.*—When sepals first divide, Madder Brown (Pl. XIII); when petals (or ray flowers) begin to unfurl, Ocher Red (Pl. XXVII); when half blown, inside of petal Pompeian Red (Pl. XIII), center of flower Chamois (Pl. XXX), and reverse of petal Buff-Yellow (Pl. IV).

*Peduncle.*—Strength—strong and rigid. Color—Grape Green (Pl. XLI), partially overlaid with Neutral Red (Pl. XXXVIII).

Bloom:

*Size.*—Approximately 2½ inches in diameter.

*Form.*—"Decorative" or Zinnia-like, with many petals (or ray flowers) compactly placed and closely overlapping.

*Texture.*—Firm.

*Fragrance.*—Lightly characteristic of usual chrysanthemum odor.

*Longevity.*—Lasts very long both on bush and as cut flower.

*Petals (or ray flowers).*—Length—medium. Opening—rather flat, except the central petals which remain spoon-shaped and partly erect until very late. Persistence—clinging.

*Color.*—Center of flower, Ochracious-Buff (Pl. XV); outer petals, Dragon's Blood Red (Pl. XIII); inside of petals, Coral Red (Pl. XIII).

Having thus disclosed my invention, I claim:

The new and distinct variety of chrysanthemum plant of the hardy, decorative type, substantially as herein shown and described, characterized particularly as to novelty by the combination of its vigorous habit of plant growth; its very healthy light-green foliage which remains on the plant all the way to the ground; its strong, upright stems; its superb flower productivity; and its medium-sized decorative type flowers of warm distinctive coloring of intense scarlet-bronze tonality derived from the blending of Dragon's Blood Red and Ochracious Buff, as indicated.

No references cited.